US012770375B2

(12) United States Patent
Chang et al.

(10) Patent No.: US 12,770,375 B2
(45) Date of Patent: Oct. 20, 2026

(54) COMPUTER DEVICE AND DEEP LEARNING METHOD OF ARTIFICIAL INTELLIGENCE MODEL FOR MEDICAL IMAGE RECOGNITION

(71) Applicants: QUANTA COMPUTER INC., Taoyuan City (TW); CHANG GUNG MEMORIAL HOSPITAL AT LINKOU, Taoyuan (TW)

(72) Inventors: Chia-Yuan Chang, Taoyuan City (TW); Chen-Hwa Sung, Taoyuan City (TW); Gigin Lin, Taoyuan (TW); Tzu-Hsiang Yang, Taoyuan City (TW); Tzu-Yun Wang, Taoyuan City (TW); Chien-Yu Huang, Taoyuan City (TW)

(73) Assignees: QUANTA COMPUTER INC., Taoyuan City (TW); CHANG GUNG MEMORIAL HOSPITAL AT LINKOU, Taoyuan (TW)

( * ) Notice: Subject to any disclaimer, the term of this patent is extended or adjusted under 35 U.S.C. 154(b) by 310 days.

(21) Appl. No.: 18/442,134

(22) Filed: Feb. 15, 2024

(65) Prior Publication Data

US 2025/0111650 A1 Apr. 3, 2025

(30) Foreign Application Priority Data

Oct. 2, 2023 (TW) ................................ 112137690

(51) Int. Cl.
*G06V 10/774* (2022.01)
*G06T 7/11* (2017.01)
(Continued)

(52) U.S. Cl.
CPC .............. *G06V 10/774* (2022.01); *G06T 7/11* (2017.01); *G06T 7/155* (2017.01); *G06T 7/174* (2017.01);
(Continued)

(58) Field of Classification Search
CPC ............ G06T 7/11; G06T 2207/30096; G06T 2207/10088; G06T 7/0012;
(Continued)

(56) References Cited

U.S. PATENT DOCUMENTS 10,489,877 B2 11/2019 Appu
11,553,874 B2 * 1/2023 Hillen .................. A61B 5/4547
(Continued)

FOREIGN PATENT DOCUMENTS

TW 201839713 A 11/2018
TW 202139075 A 10/2021

OTHER PUBLICATIONS

Lee, Wei-Meng. "Performing Image Augmentation for Machine Learning." Datature Blog, Oct. 2022, datature.io/blog/performing-image-augmentation-for-machine-learning#:~:text=Why%20is%20Image%20Augmentation%20Important,perform%20inference%20on%20unseen%20images. (Year: 2022).*

*Primary Examiner* — Sumati Lefkowitz
*Assistant Examiner* — Connor L Hansen
(74) *Attorney, Agent, or Firm* — WPAT, PC

(57) ABSTRACT

A deep learning method of an artificial intelligence model for medical image recognition is provided. The method includes the following steps: obtaining a first image set, where the first image set includes at least two images captured with different parameters; performing image pre-processing on each image of the first image set to obtain a second image set; performing image augmentation on the second image set to obtain a third image set; adding the third image set to a training image data set; and training the artificial intelligence model using the training image data set.

6 Claims, 22 Drawing Sheets

900

(51) Int. Cl.

| | |
|---|---|
| ***G06T 7/155*** | (2017.01) |
| ***G06T 7/174*** | (2017.01) |
| ***G06T 11/00*** | (2026.01) |
| ***G06V 10/26*** | (2022.01) |
| ***G06V 10/40*** | (2022.01) |
| ***G06V 20/50*** | (2022.01) |
| ***G16H 50/20*** | (2018.01) |

(52) U.S. Cl.
CPC ............ *G06T 11/00* (2013.01); *G06V 10/267* (2022.01); *G06V 10/40* (2022.01); *G06V 20/50* (2022.01); *G16H 50/20* (2018.01); *G06T 2207/10084* (2013.01); *G06T 2207/20036* (2013.01); *G06T 2207/20081* (2013.01); *G06T 2207/20084* (2013.01); *G06T 2207/30096* (2013.01); *G06V 2201/031* (2022.01)

(58) Field of Classification Search
CPC . G06T 2207/10116; G06T 2207/10081; G06T 2207/10132; G06T 2207/30004; G06T 2207/30061; G06T 2207/10104; G06T 2207/20081; G06T 2207/20084; G06T 2211/441; G06T 5/60; G06V 10/267; G06V 2201/031; G06V 2201/03; G06V 10/26; G06V 10/774; G06V 10/82
See application file for complete search history.

(56) References Cited

U.S. PATENT DOCUMENTS

| | | | | |
|---|---|---|---|---|
| 2013/0223711 A1* | 8/2013 | Knapp | ............... | G06V 10/7715 382/131 |
| 2019/0357870 A1* | 11/2019 | Madabhushi | ........ | G06V 10/764 |
| 2023/0018833 A1* | 1/2023 | Das | ........................ | G16H 50/70 |

* cited by examiner

COMPUTER DEVICE AND DEEP LEARNING METHOD OF ARTIFICIAL INTELLIGENCE MODEL FOR MEDICAL IMAGE RECOGNITION

CROSS REFERENCE TO RELATED APPLICATION

The present application is based on, and claims priority from, Taiwan Application Serial Number 112137690, filed Oct. 2, 2023, the disclosure of which is hereby incorporated by reference herein in its entirety.

BACKGROUND OF THE DISCLOSURE

1. Field of the Disclosure

The present disclosure relates to image recognition, and in particular, to a computer device and a deep learning method of an artificial intelligence model for medical image recognition.

2. Description of the Related Art

Current automatic image segmentation technologies for medical images have been developed for a period of time. However, the progress of abdominal and pelvic organ segmentation lags far behind other body parts such as brain and thorax. Main challenges encountered at present include: (1) a lack of strong and fixed bone positions in abdominal organs, resulting in greater variability in shape, size, and position of anatomical structures of interest; (2) low contrast among adjacent organs and surrounding tissues (poor edge detection effect); (3) intestinal gas, intestinal peristalsis, and respiration causing motion artifacts and image blurring; (4) high variability in organ position relative to other fixed anatomical structures; and (5) tissue changes or abnormalities possibly causing organ enlargement and/or changes in relative position.

While various methods have been attempted to solve the aforementioned problems, no suitable algorithm is currently available for image segmentation to enable abdominal organs in a medical image.

SUMMARY

Therefore, the present disclosure provides a computer device and a deep learning method of an artificial intelligence model for medical image recognition to solve the aforementioned problems. The present disclosure can overcome the limitations of conventional medical image processing algorithms such as threshold segmentation or edge segmentation to improve image segmentation of abdominal or other organs. In addition, the present disclosure can perform image segmentation in a two-dimensional or three-dimensional space based on computed tomography imaging or magnetic resonance imaging scans. Even in the presence of multiple medical image sequence slices, the present disclosure can still complete image segmentation within computational times acceptable for clinical research.

In an embodiment, the present disclosure provides a computer device, including a storage device and a processor. The storage device is configured to store an image pre-processing application and an artificial intelligence model. The processor is configured to execute the image pre-processing application and the artificial intelligence model to perform the following operations: obtaining a first image set, where the first image set includes at least two images captured with different parameters; performing image pre-processing on each image of the first image set to obtain a second image set; performing image augmentation on the second image set to obtain a third image set; adding the third image set to a training image data set; and training the artificial intelligence model using the training image data set.

In another embodiment, the present disclosure further provides a deep learning method of an artificial intelligence model for medical image recognition. The method includes the following steps: obtaining a first image set, where the first image set includes at least two images captured with different parameters; performing image pre-processing on each image of the first image set to obtain a second image set; performing image augmentation on the second image set to obtain a third image set; adding the third image set to a training image data set; and training the artificial intelligence model using the training image data set.

DETAILED DESCRIPTION

The following description is provided as embodiments for completing the present disclosure, with the purpose of describing the basic spirit of the present disclosure, but not intended to limit the present disclosure. The scope of the present disclosure is determined by reference to the appended claims.

It should be understood that terms such as "include", "comprise", and the like in the specification are used to indicate the existence of specific technical features, values, method steps, operations, elements and/or components, but do not exclude the addition of more other technical features, values, method steps, operations, elements, components, or any combination thereof.

The use of terms such as "first", "second", and "third" in the claims are used to modify component in the claims, are not intended to indicate a priority order or a precedence relationship, or one component preceding another component, or indicate a time order of executing method steps, but are only intended to distinguish components with the same name.

The phrase "configured to" can be used to describe or propose that various units, circuits, or other components are "configured to" perform one or more tasks. In such a context, the phrase "configured to" is used to imply the structure (e.g., circuit system) of those units, circuits, or components for executing the (one or more) tasks during operations. Therefore, even when a specified unit, circuit, or component is not currently operating (e.g., disconnected), it can still indicate that the specific unit/circuit/component is configured to perform the task. The units, circuits, or components used in conjunction with the phrase "configured to" include hardware, such as circuits and a memory (storing executable program instructions for implementing operations). Moreover, the phrase "configured to" may include a generic structure (e.g., a generic circuit system) that is manipulated by software and/or firmware (e.g., FPGA or general-purpose processor executing software), to operate in a manner capable of performing (one or more) tasks to be solved. The phrase "configured to" may also include adapting a manufacturing process (e.g., semiconductor manufacturing equipment) to manufacture a device (e.g., an integrated circuit) that is adapted to implement or perform one or more tasks.

Figure 1:
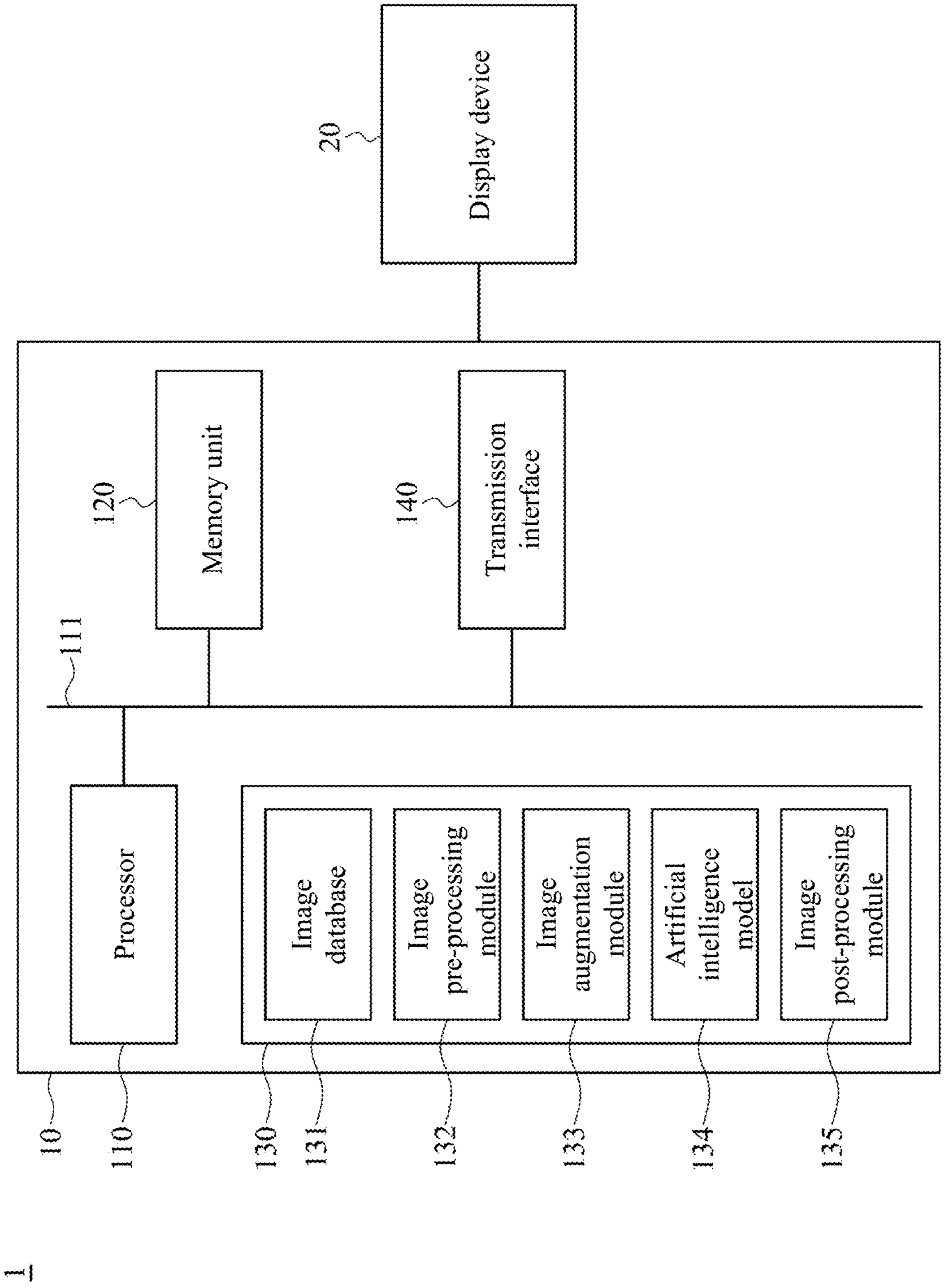
FIG. 1 is a block diagram of a computer system according to an embodiment of the present disclosure.

FIG. 1 is a block diagram of a computer system according to an embodiment of the present disclosure.

As shown in FIG. 1, the computer system 1 may include a host 10 and a display device 20, where the host 10 may be electrically connected to the display device 20. In some embodiments, the host 10 may include a processor 110, a memory unit 120, a storage device 130, and a transmission interface 140. The processor 110, the memory unit 120, the storage device 130, and the transmission interface 140 may be electrically connected through a bus 111 or other connecting member. In some embodiments, the processor 110 may include a central processing unit, a general-purpose processor, a microcontroller, an application-specific integrated circuit (ASIC), a field-programmable gate array (FPGA), or the like, but the present disclosure is not limited thereto. In some embodiments, the bus 111 may be a serial advanced technology attachment (SATA) bus, a peripheral component interconnect express (PCI Express, PCIe) bus, or the like, but the present disclosure is not limited thereto.

In some embodiments, the memory unit 120 may be a system memory of the host 10, and it may be, for example, implemented by a dynamic random access memory (DRAM), a static random access memory (SRAM), or a flash memory, but the present disclosure is not limited thereto. The memory unit 120 may be, for example, used as an execution space in which the processor 110 executes various applications or software, and it may be used as a storage space for storing temporary files or intermediate files generated when the processor 110 executes machine learning, image recognition, or various types of image processing.

In some embodiments, the storage device 130 may be a non-volatile memory, implemented using, for example, a hard disk drive (HDD), a solid-state storage device (SSD), a flash memory, a read-only memory (ROM), or the like, but the present disclosure is not limited thereto. The storage device 130 may include an image database 131, an image pre-processing module 132, an image augmentation module 133, an artificial intelligence model 134, and an image post-processing module 135, where functions of the image database 131 and the modules 132 to 135 are described below in detail.

In some embodiments, the transmission interface 140 may include a wired communication interface and/or a wireless communication interface configured to electrically connect the host 10 to the display device 20, an external arithmetic device, a cloud server, or the like, but the present disclosure is not limited thereto. For example, the wired communication interface may include a high definition multimedia interface (HDMI), a DisplayPort interface, an embedded DisplayPort (eDP) interface, a universal serial bus (USB) interface, a USB Type-C interface, a Thunderbolt interface, a digital visual interface (DVI), a video graphics array (VGA) interface, a general-purpose input/output (GPIO) interface, a universal asynchronous receiver/transmitter (UART) interface, a serial peripheral interface (SPI) interface, an inter-integrated circuit bus (I2C) interface, or a combination thereof, and a wireless transmission interface may include: a Bluetooth interface, a Wi-Fi interface, a near-field communication (NFC) interface, or the like, but the present disclosure is not limited thereto.

In some embodiments, the image database 131 may be configured to store a training image data set and a test image data set. The training image data set may include a plurality of training images, which may be original abdominal medical images (e.g., magnetic resonance imaging (MRI) images or computed tomography (CT) images) having different parameters and a plurality of augmentation training images generated by the image augmentation module 133 according to the aforementioned original abdominal medical images. The test image data set may also include a plurality of test images, which may be original abdominal medical images different from those in the training image data set. In some embodiments, the host 10 may read image data from an external image database through the transmission interface 140 and store it in the image database 131, and may also store image data from the image database 131 in the external image database through the transmission interface 140.

The image pre-processing module 132 may be configured to perform image pre-processing on a first image (or a first image set) to obtain a second image (or a second image set), where the aforementioned image pre-processing may include coordinate system conversion processing, locus-to-mask processing, image padding processing, and image normalization processing. In some embodiments, the medical images in the training image data set and the test image data set stored in the image database 131 may utilize different anatomical coordinate systems (e.g., LPS, RAS, LAS, etc.). Thus, the coordinate system conversion processing performed by the image pre-processing module 132 can convert a coordinate system of the first image (or the first image set) to a target coordinate system.

Figure 8A:
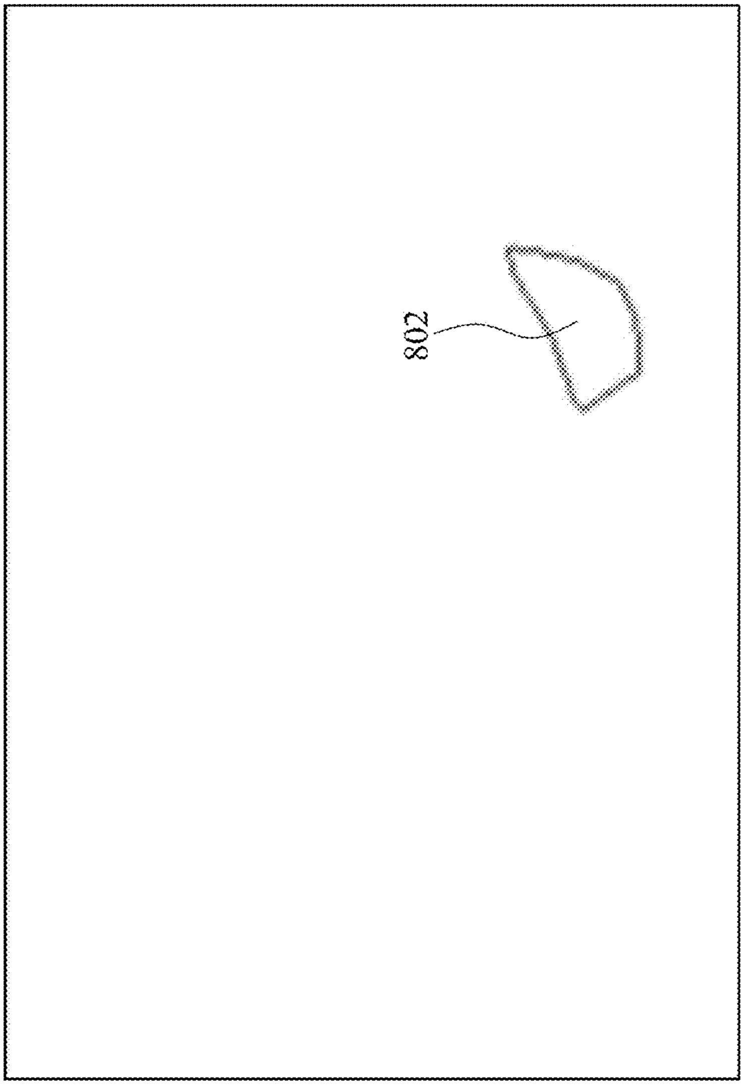
FIG. 8A is a diagram of a labeled locus according to an embodiment of the present disclosure.
Figure 8B:
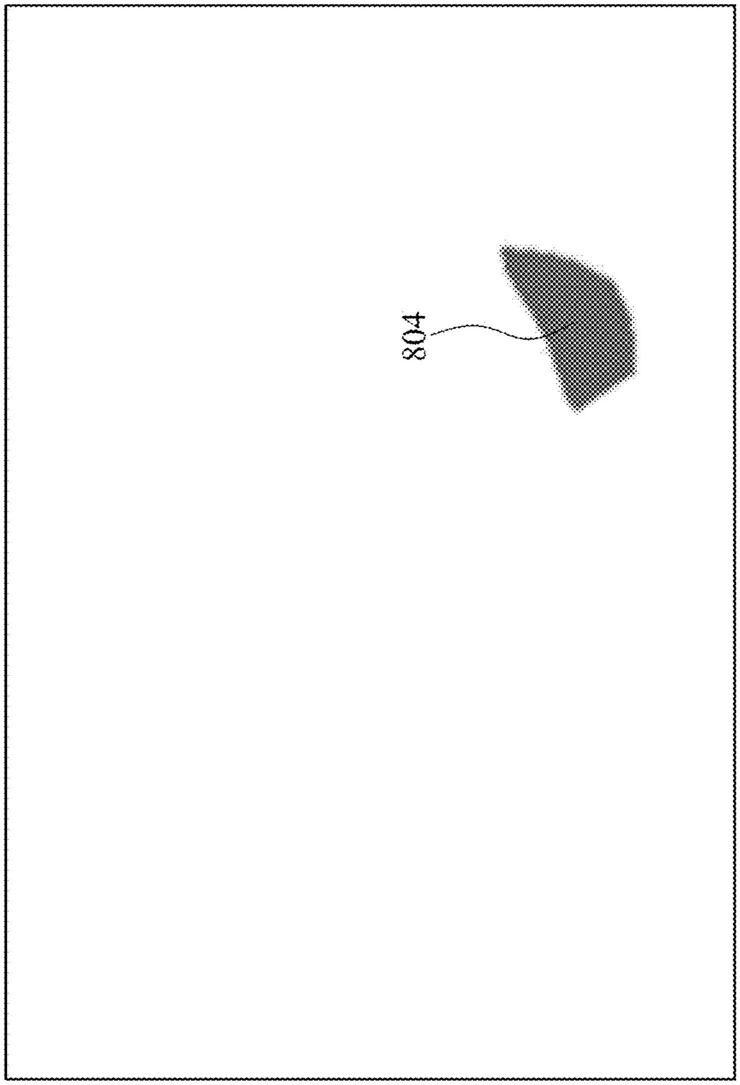
FIG. 8B is a diagram of a mask region according to the embodiment of FIG. 8A of the present disclosure.
Figure 8C:
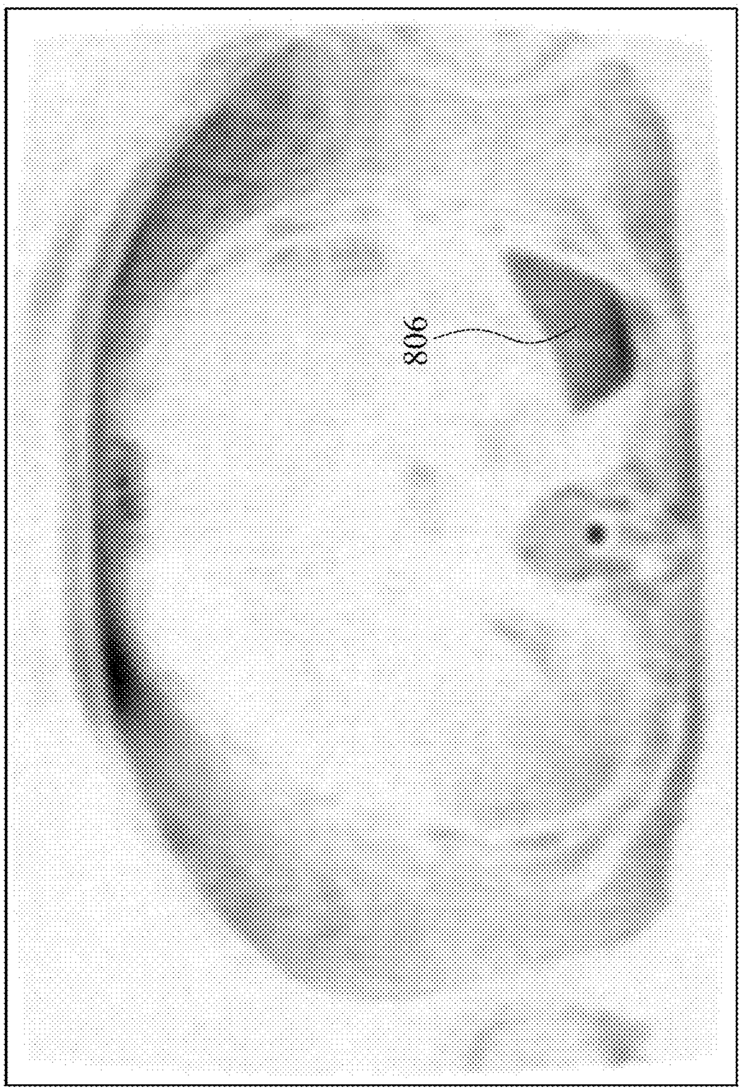
FIG. 8C is a diagram of a medical image superimposed on the mask region according to the embodiment of FIG. 8A of the present disclosure.
Figure 13C:
FIG. 13A to FIG. 13C are medical images using three different parameters according to an embodiment of the present disclosure.
Figure 13B:
Figure 13A:
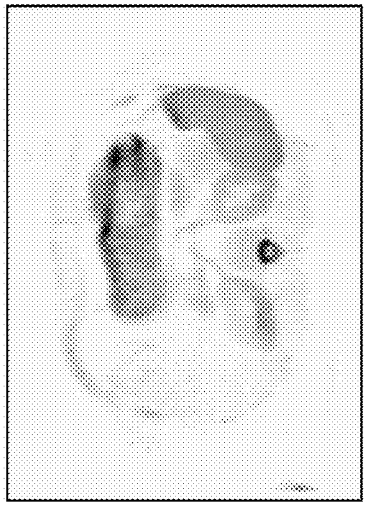
Figure 13F:
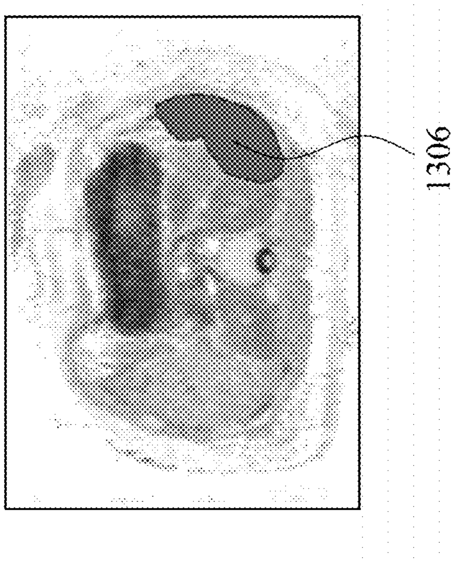
FIG. 13D to FIG. 13F are medical images superimposed on ground truth masks according to the embodiments of FIG. 13A to 13C of the present disclosure.
Figure 13E:
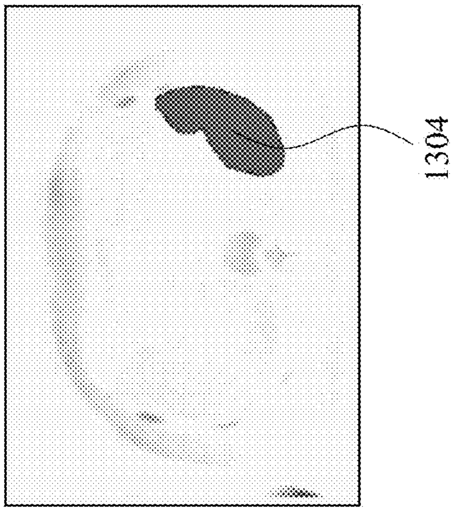
Figure 13D:
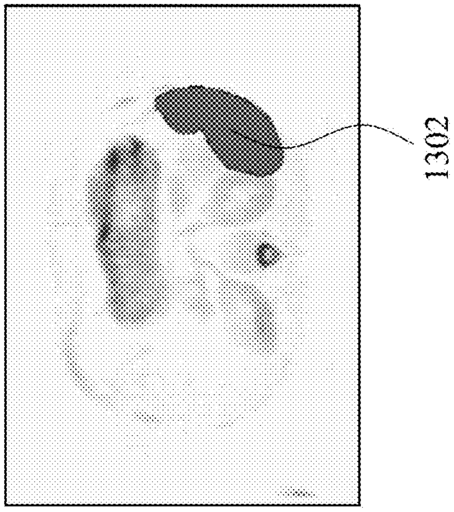
Figure 13G:
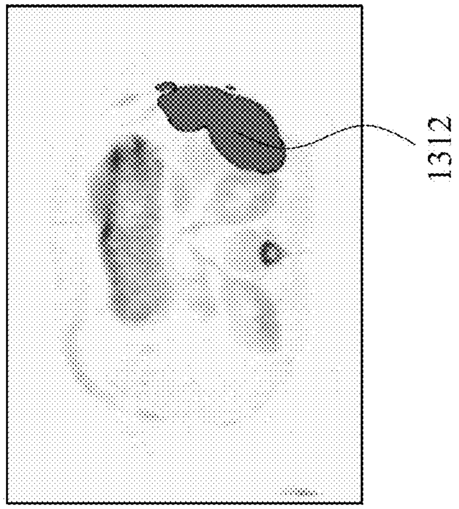
FIG. 13G to FIG. 13I are medical images superimposed on predicted masks according to the embodiments of FIG. 13A to 13C of the present disclosure.
Figure 13H:
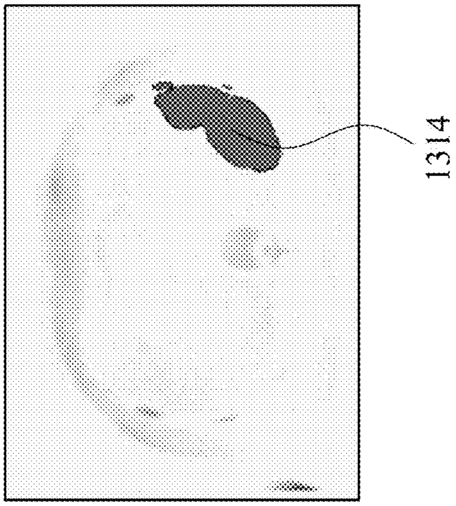
Figure 13I:
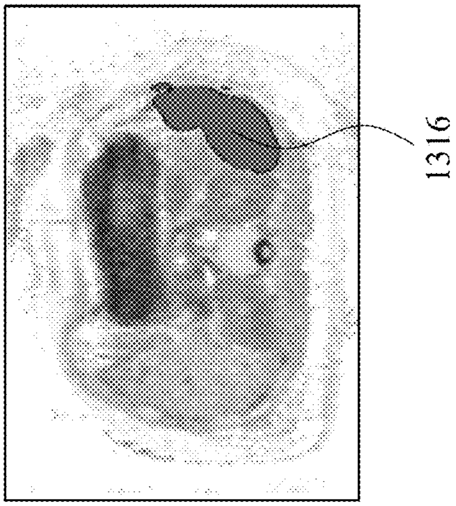

It should be noted that an organ position in each training image set in the training image data set has been labeled. Doctors often label an organ position (e.g., outline of an organ) manually from each training image (i.e., medical image) in the training image set, and a manually labeled locus forms a hollow enclosed region, as shown in locus 802 in FIG. 8A. Accordingly, the locus-to-mask processing performed by the image pre-processing module 132 may convert the labeled region to a mask (as shown by a mask region 804 in FIG. 8B), facilitating labeling of the organ position in each training image of the training image set, as shown by a mask region 806 in FIG. 8C. Specifically, when an organ position is labeled in each medical image, if only referring to a single medical image with a fixed parameter, the locus may be less accurate. If the doctors can simultaneously view a plurality of medical images of the same patient taken at substantially the same time interval and at the same location with different parameters, the doctors can make more accurate determinations and select the organ positions of the patients when viewing medical images obtained from these multiple parameters. For example, the medical images may be magnetic resonance imaging (MRI) images obtained using different imaging parameters such as b0 (e.g., b factor is equal to 0), b1000 (e.g., b factor is equal to 1000) imaging, or apparent diffusion coefficient (ADC). The images obtained using the imaging parameters b0, b1000, and ADC may be respectively shown in FIG. 13A, FIG. 13B, and FIG. 13C. For example, in FIG. 13D, FIG. 13E, and FIG. 13F, the doctors respectively label regions 1302, 1304, and 1306 (also known as ground truth masks) from FIG. 13A, FIG. 13B, and FIG. 13C to represent corresponding organ regions. In addition, predicted masks recognized by the artificial intelligence model 134 from input images in FIG. 13A to FIG. 13C are shown by regions 1312, 1314, and 1316 in FIG. 13G, FIG. 13H, and FIG. 13I, respectively.

In the present disclosure, when the doctor simultaneously views each training image in the training image set, the doctor can determine and label the patient's organ position in each training image in the training image set. Thus, the labeled organ region in each training image of the training image set for the artificial intelligence model 134 can be obtained. If the artificial intelligence model 134 is in an object recognition phase, the locus to mask processing in the image pre-processing can be omitted.

In some embodiments, training images required by the artificial intelligence model 134 in a training phase or input images in the recognition phase may be square images, for example, with a resolution of 256×256 pixels. However, training images in the training image data set or input images in the recognition phase may be rectangular images instead of square images. Accordingly, the image pre-processing module 132 can perform the image padding processing to convert the rectangular images to square images. For example, pixels can be padded on the shorter sides of the rectangular images. In some embodiments, the padded pixels can be black pixels (e.g., grayscale value=0) or white pixels (e.g., grayscale value=255). In some other embodiments, the image padding processing can be performed by mirroring or duplicating edge pixels. The image padding of the present disclosure is not limited to that disclosed. If the input image is a square image, the image pre-processing module 132 may skip this step of image padding processing.

In some embodiments, the image pre-processing module 132 may further perform the image normalization processing on the output image generated by the image padding processing. Specifically, each medical image in the image database 131 has a corresponding actual size, that is, each pixel in each medical image has corresponding dimensions (including actual length, width, or height). The image normalization processing performed by the image pre-processing module 132 can normalize the output image for consistent dimensions of the normalized output images.

The image augmentation module 133 may be configured to perform the image augmentation processing on one or more input images to obtain a plurality of output images, where the number of the output images is greater than the number of the input images. For example, in the training phase of the artificial intelligence model 134, a large number of training images is required to achieve better image recognition without overfitting. However, the number of medical images (including magnetic resonance imaging images and computed tomography images) obtained by photographing a specific body part of the same patient is often quite limited. Furthermore, because medical images may invoke privacy issues of patients, for which authorization may be required, thereby further limiting the number of images available for training the artificial intelligence model 134. If only a small number of actually captured medical images are used as training images, the artificial intelligence model 134 may fail to achieve good image recognition due to overfitting.

In some embodiments, the image augmentation processing performed by the image augmentation module 133 may include: rotation, shearing, flipping, mirroring, clipping, scaling, brightness adjustment, contrast adjustment, and the like, but the present disclosure is not limited thereto. For example, the image augmentation module 133 may receive the normalized image (or image set) generated by the image pre-processing module 132 as the input image thereof, and perform the aforementioned image augmentation processing on the input image (or image set) to obtain a plurality of output images. The aforementioned output images (or image set) can be stored in the training image data set of the image database 131 as training data for the artificial intelligence model 134. Therefore, the image augmentation processing performed by the image augmentation module 133 can increase the number of training images to meet the requirement of the artificial intelligence model 134 in the training phase.

In some embodiments, the artificial intelligence model 134 may be, for example, a convolutional neural network (CNN) or deep neural network (DNN) or an extended artificial intelligence model such as UNet, UNet_leak, UNet_leak_3D, Attention_Unet, R2UNet, ResNet34, or the like, but the present disclosure is not limited thereto. The artificial intelligence model 134 can be trained using the training image data set in the image database 131 through the deep learning method proposed in the present disclosure, and tested for object recognition using the test image data set in the image database 131, where the training image data set includes a plurality of image sets. It should be noted that in the training phase, the artificial intelligence model 134 can receive a plurality of image sets for training, each image set of which may include at least two training images with different parameters. For example, the first image set may be at least two medical images of patient A's same body part taken with different parameters, the second image set may be at least two medical images of patient B's same body part taken with the same at least two parameters, and so on. It should be noted that the aforementioned at least two medical images with different parameters can be original medical images obtained from imaging or processed medical images, and the medical images include but are not limited to computed tomography images, magnetic resonance imaging images, fluoroscopy images, ultrasonic images, and the like.

In an embodiment, for ease of description, three training images are used as an example of the aforementioned at least two training images. The aforementioned at least two training images with different parameters can be obtained by magnetic resonance imaging diffusion-weighted imaging on the same body part of the same patient during substantially the same time interval using b0, b1000, and ADC parameters, respectively, The training images can be seen in FIG. 4A, FIG. 4B, and FIG. 4C, respectively. If two training images are used, training images with any two of the b0, b1000, and ADC parameters can be used. In another embodiment, the aforementioned at least two training images with different parameters can be obtained by magnetic resonance imaging (or computed tomography) on the same body part of the same patient during substantially the same time interval and performing processing using parameters such as cerebral blood volume (CBV), cerebral blood flow (CBF), and mean transit time (MTT), respectively. The training images can be seen in FIG. 5A, FIG. 5B, and FIG. 5C, respectively. If two training images are used, training images with any two of the CBV, CBF, and MTT parameters can be used.

Figure 5A:
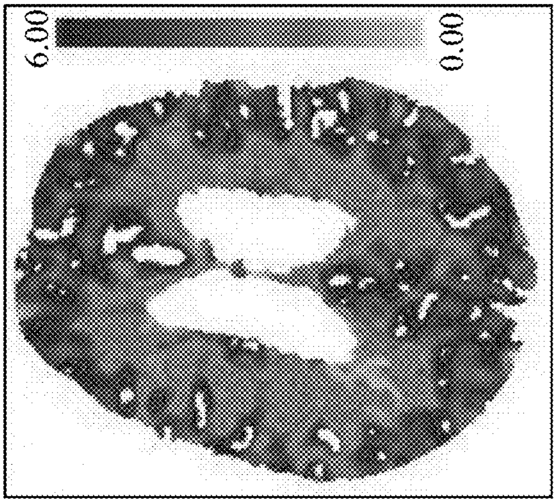
FIG. 5A to FIG. 5C are medical images using three different parameters according to another embodiment of the present disclosure.
Figure 5B:
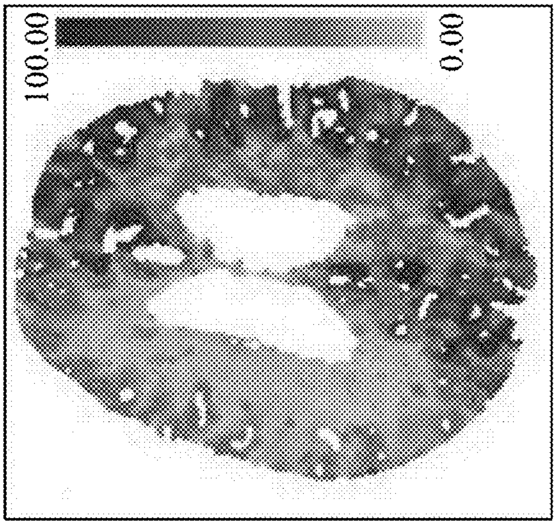
Figure 5C:
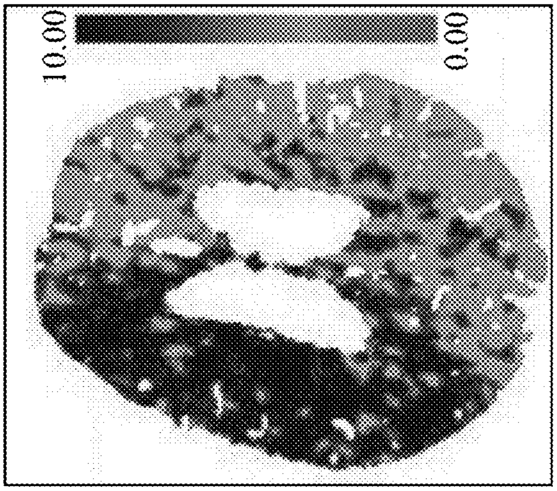
Figure 6A:
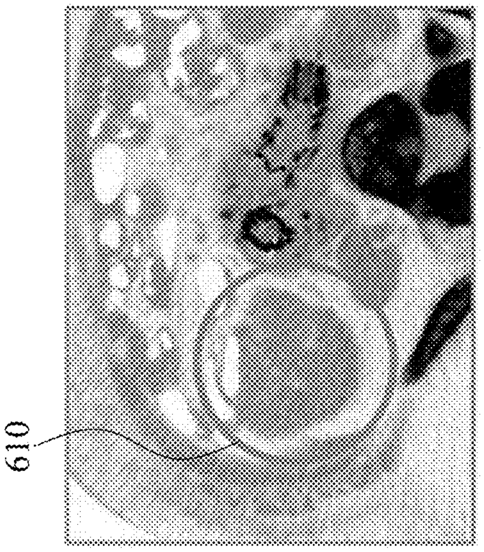
FIG. 6A to FIG. 6C are medical images using three different parameters according to yet another embodiment of the present disclosure.
Figure 6B:
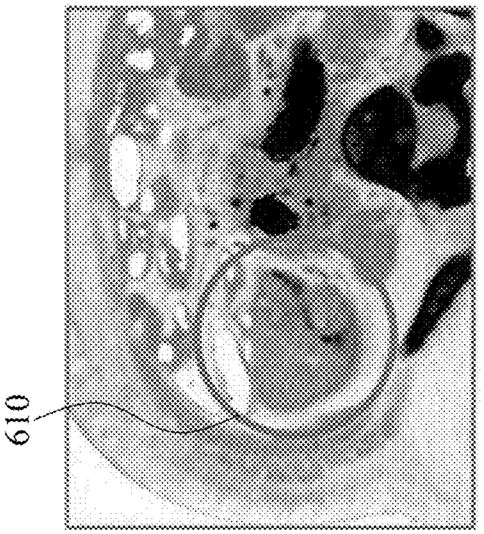
Figure 6C:
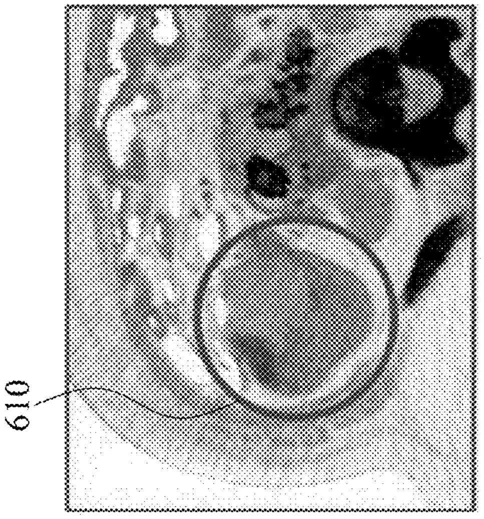
Figure 7C:
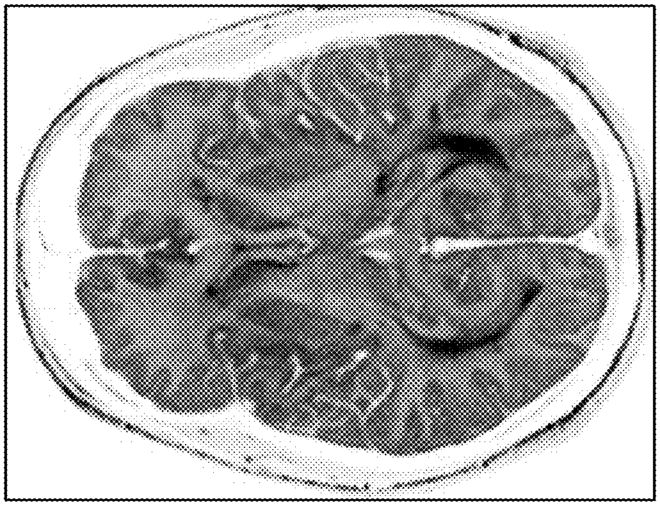
FIG. 7A to FIG. 7C are medical images using three different parameters according to still another embodiment of the present disclosure.
Figure 7B:
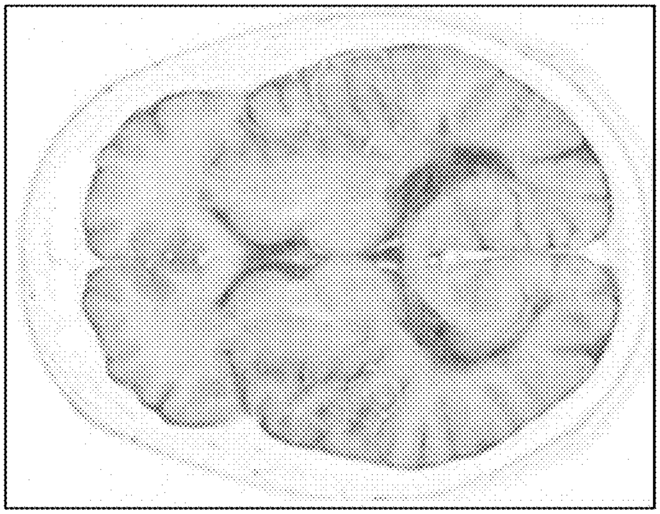
Figure 7A:
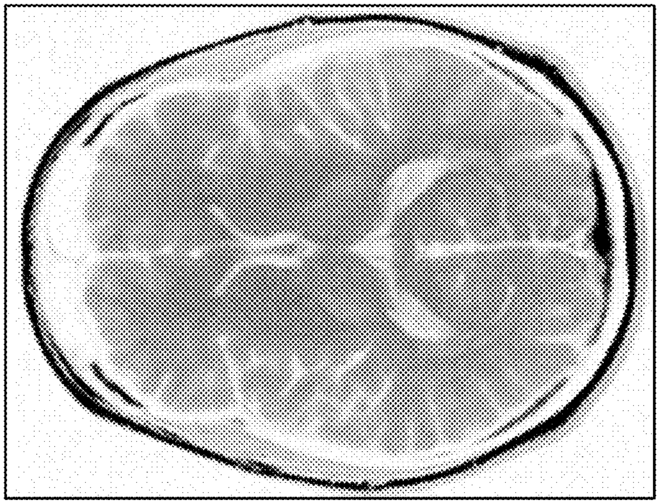

In yet another embodiment, the aforementioned at least two training images with different parameters can be obtained by computed tomography on the same body part of the same patient during substantially the same time interval using parameters such as no-contrast, contrast-arterial phase, and contrast-portal venous phase, respectively. The training images can be seen in FIG. 6A, FIG. 6B, and FIG. 6C, respectively, with the body part indicated by region 610. For example, a computed tomography scanner may scan the patient to obtain a no-contrast computed tomography image (as shown in FIG. 6A). Then, after injecting a contrast agent into the patient, the computed tomography scanner may scan the patient again to obtain a contrast-arterial phase computed tomography image (as shown in FIG. 6B), and then scan the patient after a period of time to obtain a contrast-portal venous phase computed tomography image (as shown in FIG. 6C). If two training images are used, training images with any two of the no-contrast, contrast-arterial phase, and contrast-portal venous phase parameters may be used. In yet another embodiment, the aforementioned at least two training images with different parameters can be obtained by magnetic resonance imaging on the same body part of the same patient in substantially the same time interval using parameters such as T1 signal, T2 signal, and proton density, respectively. The training images are shown in FIG. 7A, FIG. 7B, and FIG. 7C, respectively. If two training images are used, training images with any two of the T1 signal, T2 signal, and proton density parameters may be used. The "same time intervals" in the embodiments of FIG. 4 to FIG. 7 can vary from tens of seconds to tens of minutes, depending on the imaging method and parameters used. It should be noted that types of the medical images used in the present disclosure are not limited to the computed tomography images or magnetic resonance imaging images using different parameters as described in the embodiments of FIG. 4 to FIG. 7, and can also include fluoroscopy images, ultrasonic images, and the like using different parameters.

After performing object recognition on the input image, the artificial intelligence model 134 generates a predicted mask. The predicted mask may indicate the preliminary organ position predicted by the artificial intelligence model 134.

The image post-processing module 135 may be configured to perform image post-processing on the input image of the artificial intelligence model 134 according to the predicted mask generated by the artificial intelligence model 134 to obtain an image post-processing region, and to calculate an overlapping region between the image post-processing region and the predicted mask to obtain a target organ region. The image post-processing performed by the image post-processing module 135 is detailed in the embodiment of FIG. 11.

Figure 2:
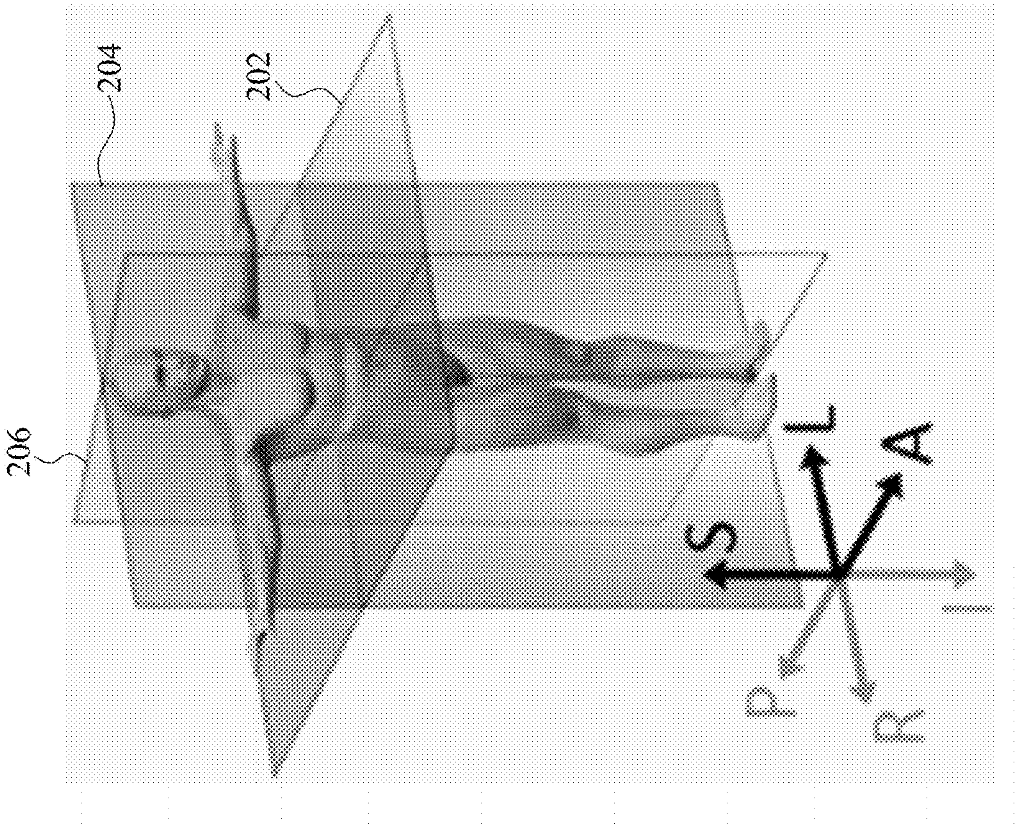
FIG. 2 is a diagram of an anatomical coordinate system according to an embodiment of the present disclosure.
Figure 3A:
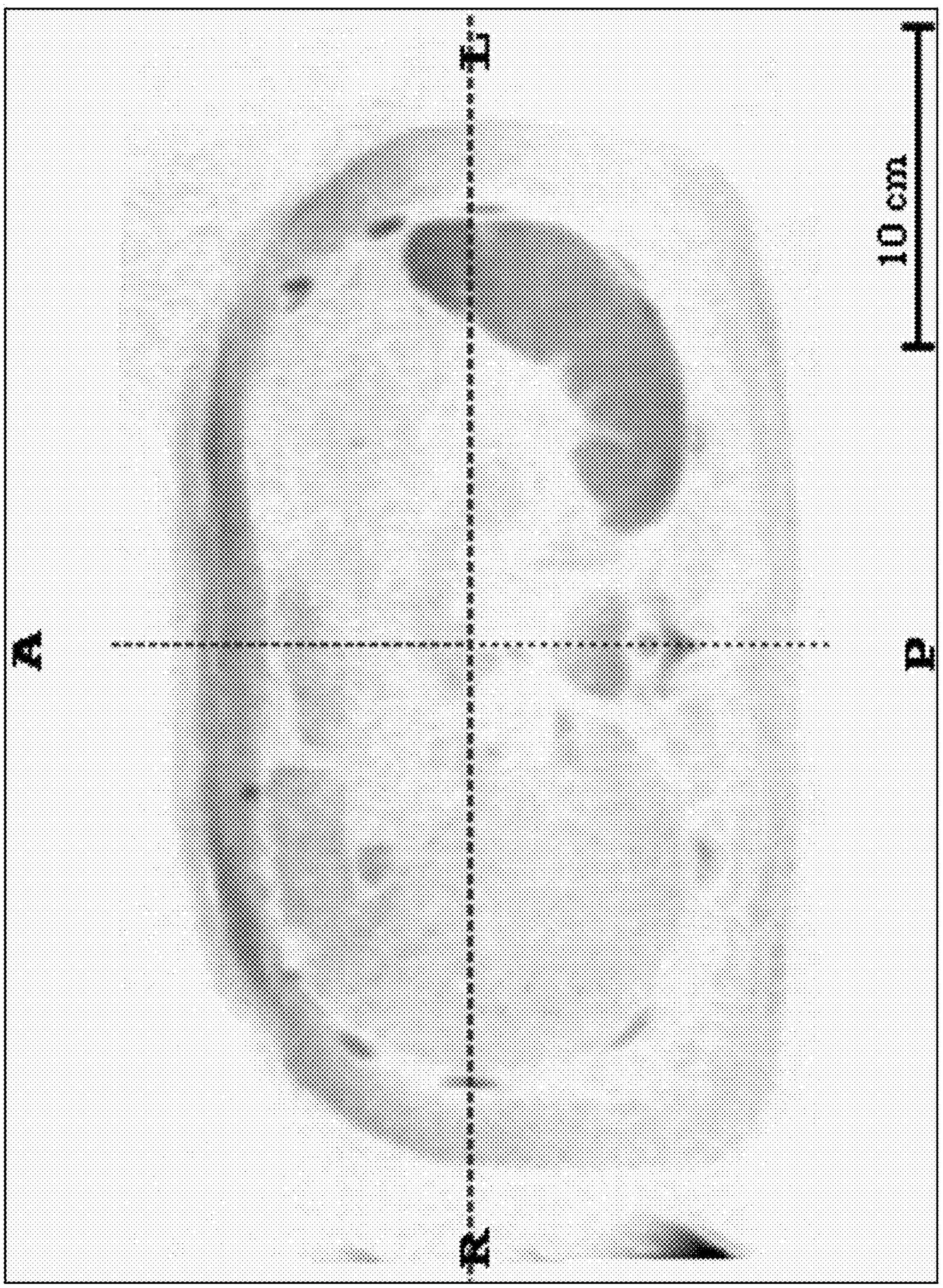
FIG. 3A to FIG. 3C are different medical images according to an embodiment of the present disclosure.
Figure 3B:
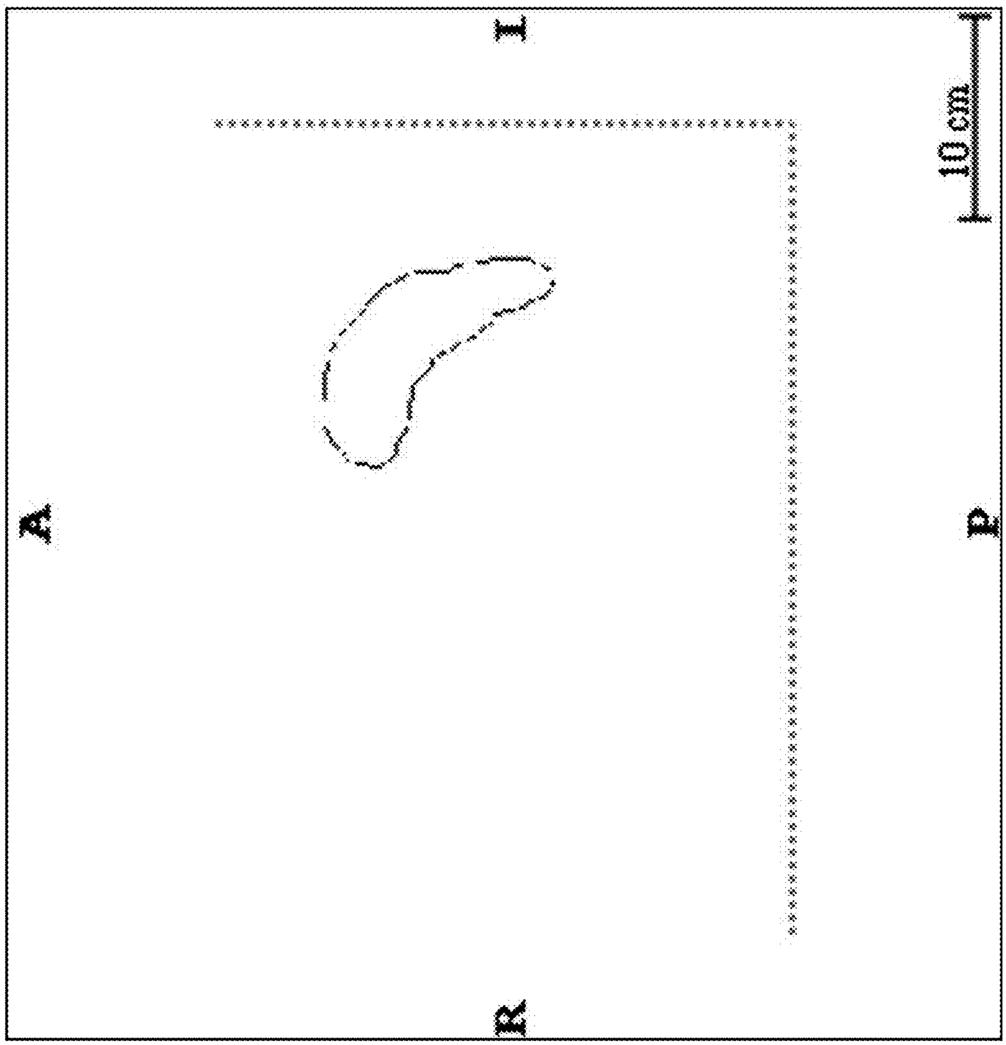
Figure 3C:
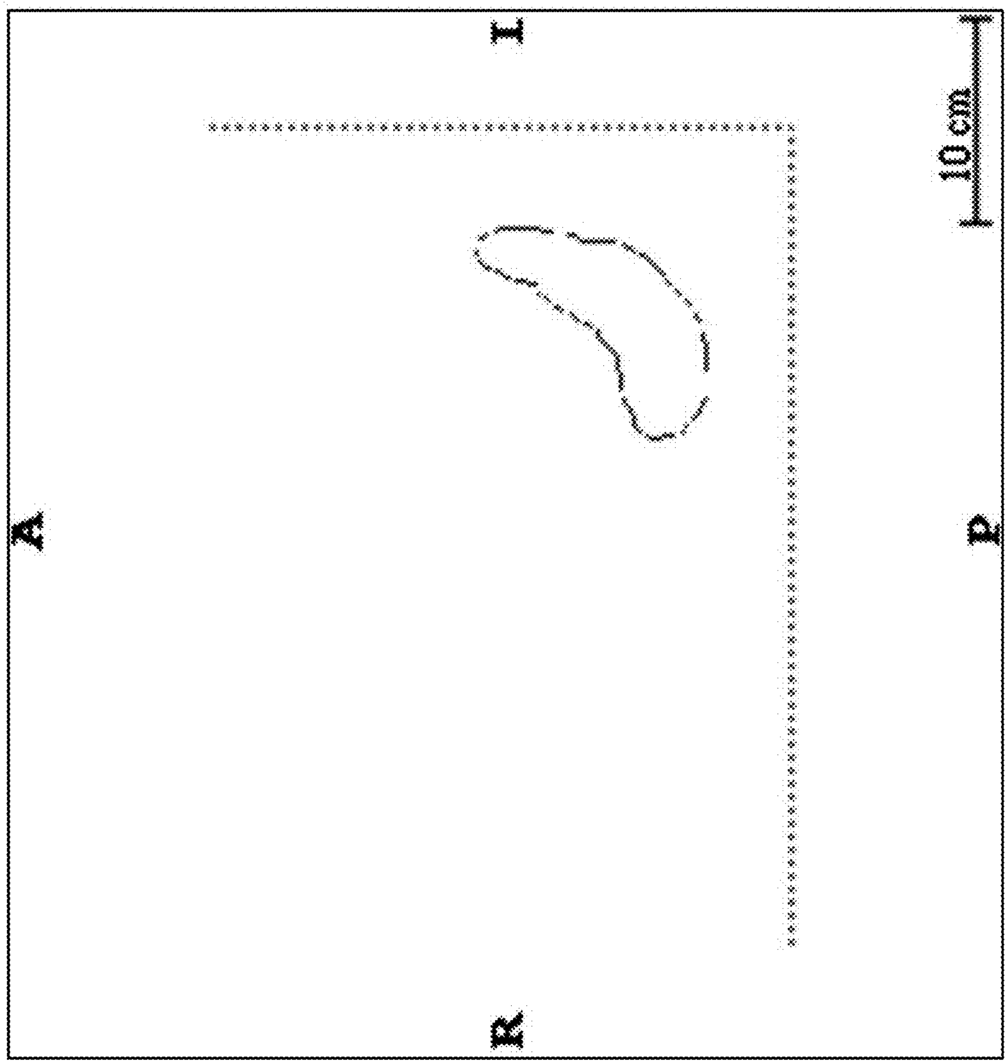

FIG. 2 is a diagram of an anatomical coordinate system according to an embodiment of the present disclosure. FIG. 3A to FIG. 3C are diagrams of different medical images according to an embodiment of the present disclosure.

In some embodiments, an anatomical coordinate system may be composed by three planes such as an axial plane 202, a coronal plane 204, and a sagittal plane 206. The axial plane 202 is parallel to the ground (i.e., horizontal), and divides a human body into head (superior) and feet (inferior). The coronal plane 204 is perpendicular to the ground (i.e., vertical), and divides the human body into front (anterior) and back (posterior). The sagittal plane 206 is perpendicular to the ground, and divides the human body into left and right. Through the axial plane 202, the coronal plane 204, and the sagittal plane 206, the anatomical coordinate system can have six positively described axes, S (superior), I (inferior), A (anterior), P (posterior), L (left), and R (right), the axes further paired into S-I, A-P, and L-R. In addition, different anatomical coordinate systems commonly used by different medical departments. The three-dimensional coordinates in the anatomical coordinate system do not use fixed coordinate axes, and different medical application software may use different coordinate axes. For example, MHD image, ITK tool kit, and ITK-Snap software use the LPS (Left, Posterior, Superior) coordinate system. The Nifti image and 3D Slicer software use the RAS (Right, Anterior, and Superior) coordinate system.

FIG. 3A and FIG. 3B illustrate different magnetic resonance imaging images using the LPS coordinate system, and FIG. 3C illustrates a magnetic resonance imaging image using the RAS coordinate system, wherein corresponding anatomical coordinate axes are marked in the upper, lower, left, and right directions in FIG. 3A to FIG. 3C. For example, after FIG. 3B undergoes coordinate axis conversion by the image pre-processing module 132, the LPS coordinate system shown in FIG. 3B can be converted to the RAS coordinate system shown in FIG. 3C. It should be noted that each of FIG. 3A to FIG. 3C includes a scale to indicate a corresponding actual length, width, or height thereof.

Figure 9:
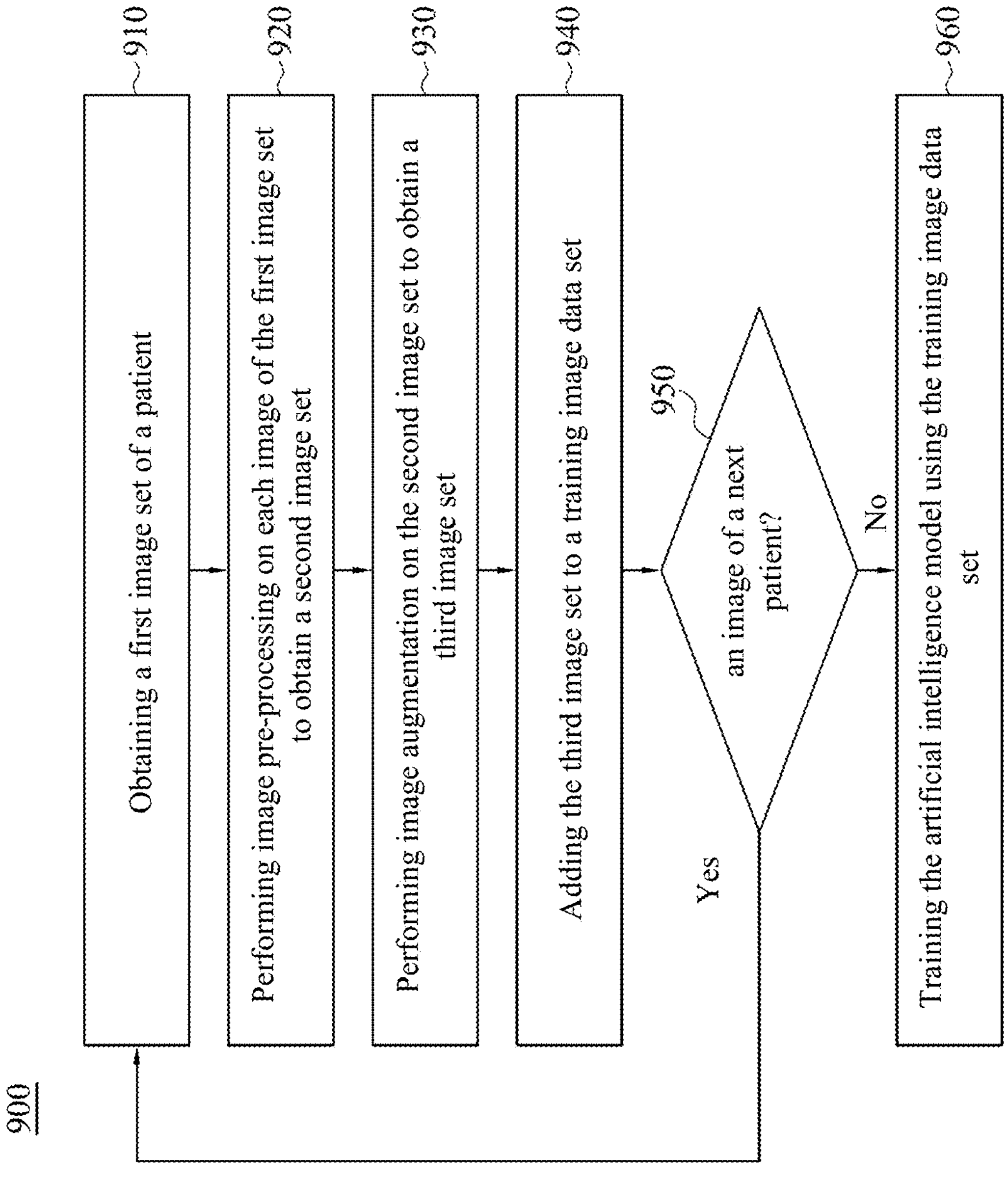
FIG. 9 is a flowchart of a deep learning method 900 of an artificial intelligence model for medical image recognition according to an embodiment of the present disclosure.

FIG. 9 is a flowchart of a deep learning method 900 of an artificial intelligence model for medical image recognition according to an embodiment of the present disclosure. Please refer to both FIG. 1 and FIG. 9.

Figure 4C:
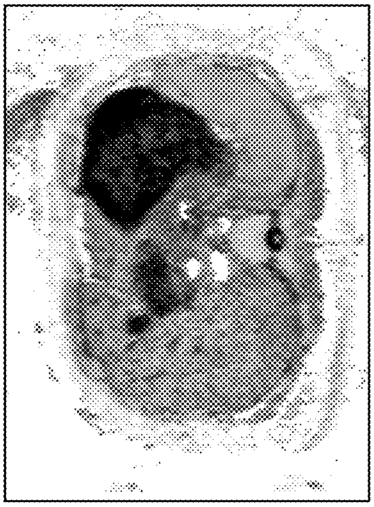
FIG. 4A to FIG. 4C are medical images using three different parameters according to an embodiment of the present disclosure.
Figure 4B:
Figure 4A:
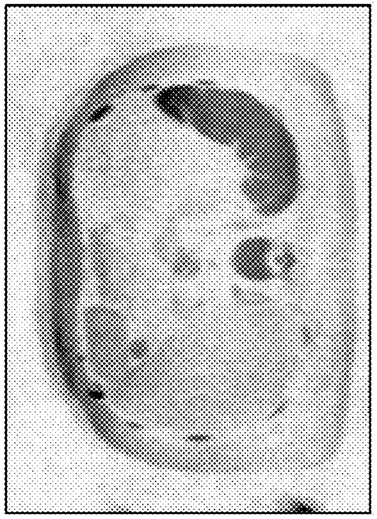

Step 910: Obtaining a first image set of a patient. For example, the first image set may include at least two medical images obtained by photographing the same body part of the same patient during substantially the same time interval with different parameters. For example, FIG. 4A to FIG. 4C illustrate magnetic resonance images obtained by photographing the same location on the abdomen of the same patient during substantially the same time interval with three different parameters. FIG. 5A to FIG. 5C illustrate magnetic resonance images obtained by photographing the same location on the brain of the same patient during substantially the same time interval with three different parameters. FIG. 6A to FIG. 6C are computed tomography images obtained by photographing the same location on the abdomen of the same patient during substantially the same time interval with three different parameters. FIG. 7A to FIG. 7C are magnetic resonance images obtained by photographing the same location on the brain of the same patient during substantially the same time interval with three different parameters. If two medical images are used, medical images with any two of the aforementioned parameters may be used. For details thereof, reference may be made to related descriptions of the embodiments of FIG. 4A to FIG. 4C, FIG. 5A to FIG. 5C, FIG. 6A to FIG. 6C, and FIG. 7A to FIG. 7C. In some embodiments, each image in the first image set has been labeled with a corresponding labeled organ region (or referred to as ground truth mask) by medical personnel. In some other embodiments, each image in the first image set may be input to the trained artificial intelligence model 134, with each image different from the training images previously used for training the artificial intelligence model 134. The artificial intelligence model 134 may mark the labeled organ region in each image in the first image set, and the medical personnel can further select training images from the first image set for re-training the artificial intelligence model 134.

Step 920: Performing image pre-processing on each image of the first image set to obtain a second image set. For example, the image pre-processing may include coordinate system conversion processing, locus-to-mask processing (e.g., converting a locus labeled by the medical personnel into a ground truth mask), image padding processing, image normalization processing, or a combination thereof. In some embodiments, because each image (e.g., a three-dimensional image with at least two images overlaid) in the first image set may include at least two medical images (e.g., magnetic resonance imaging images or computed tomography images) obtained by photographing the same body part of the same patient using different parameters, the image pre-processing performed by the image pre-processing module 132 on each image in the first image set is consistent.

Step 930: Performing image augmentation processing on the second image set to generate a third image set. The number of images in the third image set is greater than that in the second image set. For example, in the training phase of the artificial intelligence model 134, a large number of training images are often required to achieve a better image recognition effect without overfitting. However, the number of medical images (including magnetic resonance imaging images and computed tomography images) obtained by photographing a specific body part of the same patient is often quite limited. Furthermore, medical images may invoke privacy issues of patients for which authorization may be required, thereby further limiting the number of images available for training the artificial intelligence model 134. If only a small number of actually captured medical images are used as training images, the artificial intelligence model 134 may fail to achieve a good image recognition effect due to overfitting. The image augmentation processing performed by the image augmentation module 133 may include: rotation, shearing, flipping, mirroring, clipping, scaling, brightness adjustment, contrast adjustment, and the like, but the present disclosure is not limited thereto. The image augmentation processing performed by the image augmentation module 133 can increase the number of training images, to meet the training image quantity requirement of the artificial intelligence model 134 in the training phase, thereby reducing overfitting.

Step 940: Adding the third image set to a training image data set, where the training image data set is used for training the artificial intelligence model 134.

Step 950: Determining whether there is an image of a next patient. More specifically, in step 950, it is determined whether an image of the next patient can be added to the training image data set. If an image of the next patient can be added to the training image data set, step 910 to step 940 are performed for the image of the next patient. Therefore, the training image data set may include images of one or more patients. For example, the training image data set may include a plurality of third image sets, and each third image set is derived from the corresponding first image set, where each first image set includes at least two medical images obtained by photographing the same body part of the same patient during substantially the same time interval with different parameters.

If it is determined in step 950 that no image of the next patient can be added to the training image data set, step 960 is performed. Step 960: Training the artificial intelligence model 134 based on the existing training image data set. In some embodiments, if the artificial intelligence model 134 (e.g., version 1) has already been trained and each image in the first image set is different from the training images previously used for training the artificial intelligence model 134 (e.g., version 1), the artificial intelligence model 134 (e.g., version 2) obtained after re-training in step 960 will have different weights from the previously trained artificial intelligence model 134 (e.g., version 1).

Doctors or medical personnel can simultaneously view each medical image in each image set to determine and label the organ position of patients in the training image set. In the training phase of the artificial intelligence model 134, the artificial intelligence model 134 may receive a training image data set including images of a plurality of patients for training, where the images of each patient include at least two medical images generated with different parameters. Therefore, the artificial intelligence model 134 trained using the aforementioned deep learning method can effectively reduce overfitting and achieve a better object recognition effect.

Figure 10:
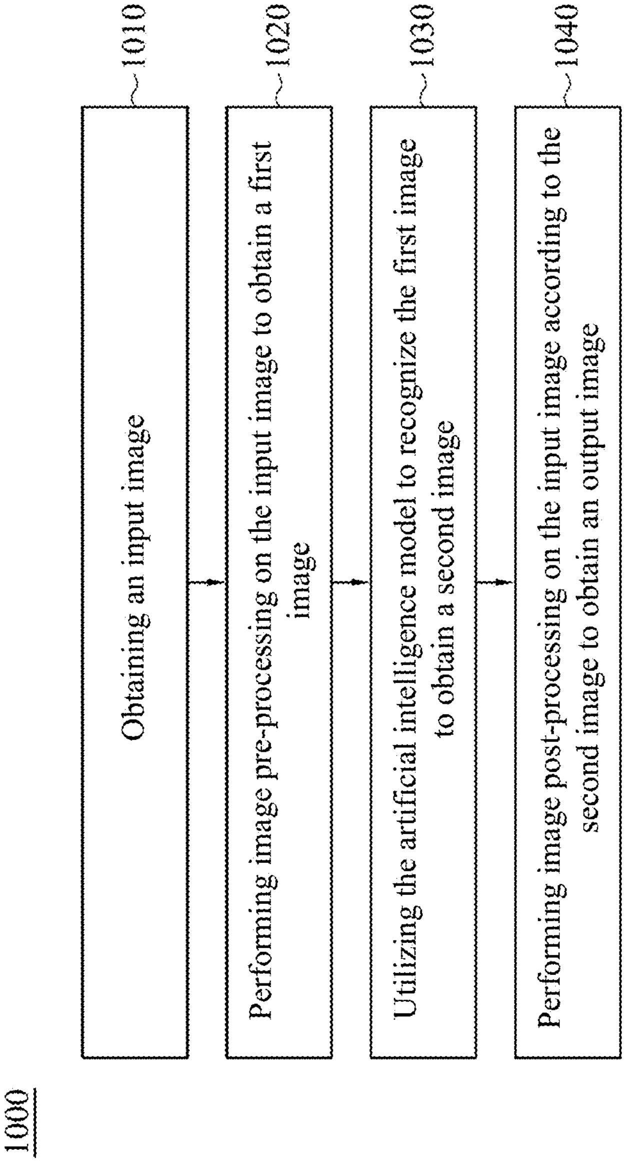
FIG. 10 is a flowchart of an object recognition method 1000 for an artificial intelligence model according to an embodiment of the present disclosure.

FIG. 10 is a flowchart of an object recognition method 1000 for an artificial intelligence model according to an embodiment of the present disclosure.

Step 1010: Obtaining an input image. For example, in an object recognition phase of the artificial intelligence model 134, an input image thereof may be a medical image obtained by photographing a specific body part of a patient with a single parameter, rather than at least two medical images obtained by photographing the same body part of the same patient during substantially the same time interval with different parameters.

Step 1020: Performing image pre-processing on the input image to obtain a first image. For example, the artificial intelligence model 134 may have a specific requirement for the input image thereof, and in the object recognition phase of the artificial intelligence model 134, the image pre-processing module 132 performs coordinate system conversion processing, image padding processing, and/or image normalization processing on the input image to obtain the first image.

Step 1030: Recognizing the first image using the artificial intelligence model 134 to obtain a second image. For example, the first image may be the image input to the artificial intelligence model 134. After the first image undergoes object recognition by the artificial intelligence model 134, the artificial intelligence model 134 generates a predicted mask of the first image as the second image. The predicted mask or the second image may indicate an organ position predicted by the artificial intelligence model 134. In some other embodiments, the artificial intelligence model 134 used in step 1030 may be an artificial intelligence model retrained through the process in FIG. 9, and the process in FIG. 9 can be repeated. For example, the artificial intelligence model 134 labels each image in a new first image set, allowing the medical personnel to select images from the new first image set for retraining the artificial intelligence model 134. In addition, each time the process in FIG. 9 is repeated, different versions of the artificial intelligence model 134 can be obtained.

In some other embodiments, the processor 110 can also calculate an actual volume corresponding to the second image, allowing the medical personnel to determine whether there is swelling of the organ in the target region image. In addition, the processor 110 may also calculate homogeneity and heterogeneity of the human body tissue in the second image, allowing the medical personnel to determine whether there is a tumor in the organ in the second image.

Step 1040: Performing image post-processing on the input image according to the second image to obtain an output image. For example, the image post-processing module 135 may be configured to perform image post-processing on the input image of the artificial intelligence model 134 according to the predicted mask generated by the artificial intelligence model 134 to obtain an image post-processing region, and to calculate an overlapping region between the image post-processing region and the predicted mask to obtain a target organ region. The image post-processing module 135 superimposes the target organ region onto the input image of the artificial intelligence model 134 to obtain the output image.

Figure 11:
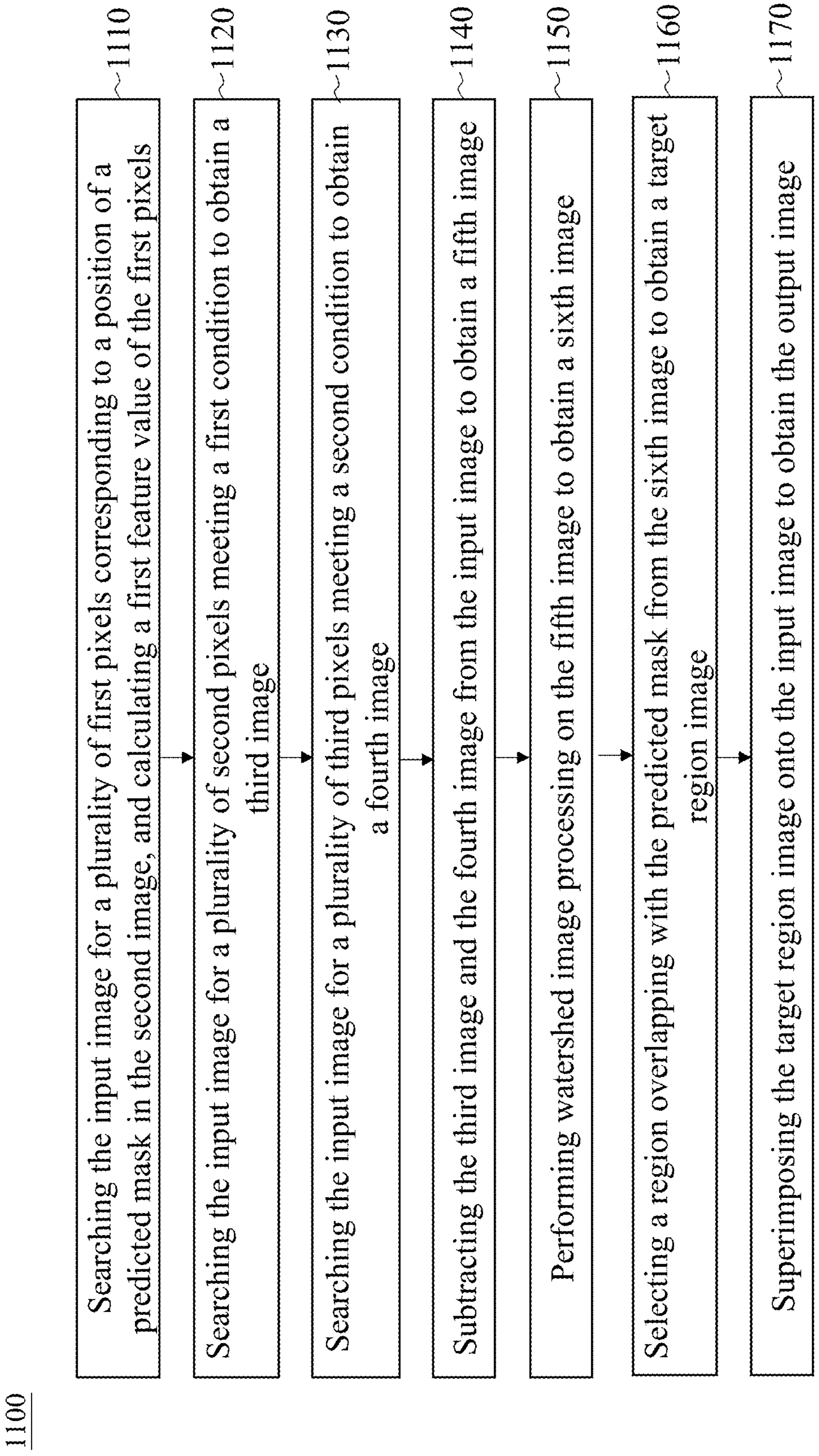
FIG. 11 is a flowchart of an image post-processing method 1100 according to the embodiment of FIG. 10 of the present disclosure.

FIG. 11 is a flowchart of an image post-processing method 1100 according to the embodiment of FIG. 10 of the present disclosure. FIG. 12A to FIG. 12G are various images in the embodiment of FIG. 11 of the present disclosure.

Please refer to FIG. 1, and FIG. 10 to FIG. 12. Step 1040 in FIG. 10 may include the image post-processing method 1100 in FIG. 11. The image post-processing method 1100 may further include steps 1110 to 1170.

Figure 12B:
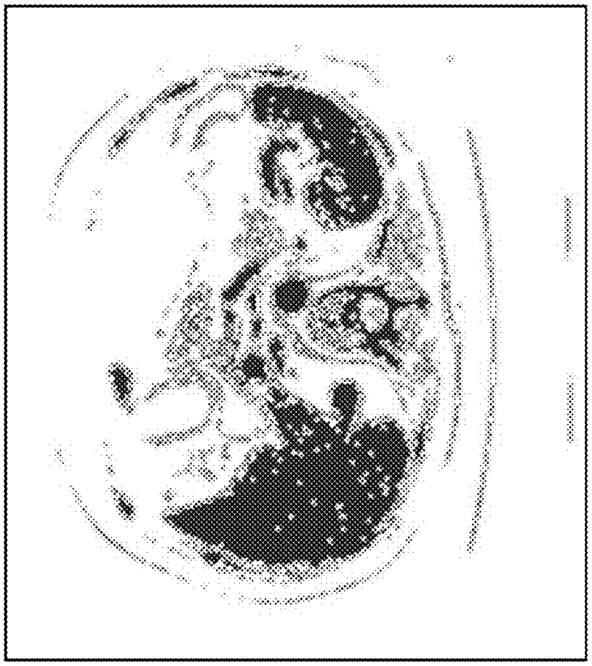
FIG. 12A to FIG. 12G are various images according to the embodiment of FIG. 11 of the present disclosure.
Figure 12A:
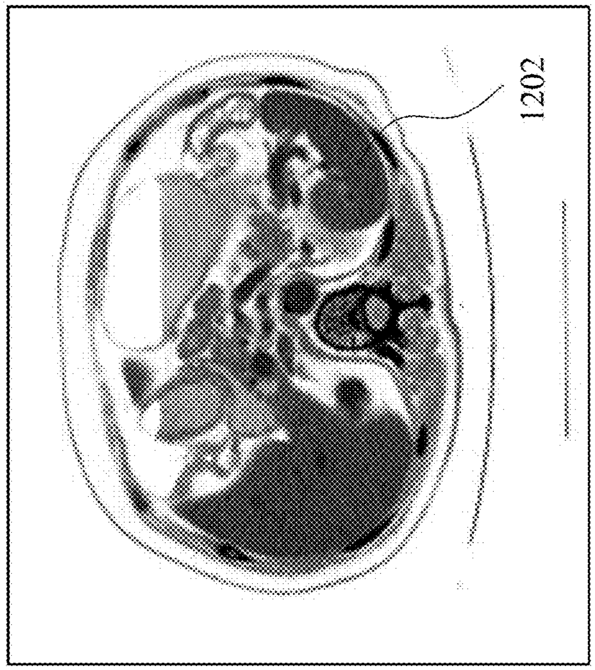

Step 1110: Searching the input image for a plurality of first pixels corresponding to a position of the predicted mask in the second image, and calculating a first feature value of the first pixels. An exemplary input image is shown in FIG. 12A, and the predicted mask is shown by region 1202 therein. That is, the image post-processing module 135 calculates the first feature value of the first pixels in the region 1202, where the first feature value may be, for example, a median value, an average grayscale value, a gradient, or a percentile (for example, brightness is within the top X %) of the first pixel.

Step 1120: Searching the input image for a plurality of second pixels satisfying a first condition to obtain a third image. In some embodiments, when the first feature value is a median value or an average grayscale value of the first pixels, the first condition is, for example, greater than the first feature value F multiplied by a predetermined threshold T1 (i.e., ">(F×T1)"). That is, the image post-processing module 135 will search the input image for the second pixels with grayscale values greater than the first feature value F multiplied by the predetermined threshold T1. In some other embodiments, when the first feature value is a gradient or a percentile of the first pixels, the first condition is, for example, the gradient or percentile greater than the predetermined threshold T1. That is, the image post-processing module 135 searches the input image for the second pixels with the gradient or percentile greater than the predetermined threshold T1. For ease of description, the first feature value is the average grayscale value of the first pixels, and the third image is shown in FIG. 12B.

Figure 12D:
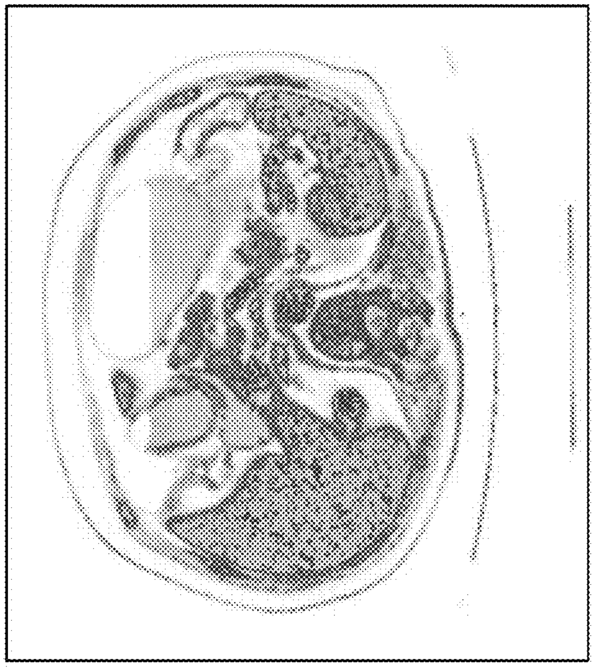
Figure 12C:
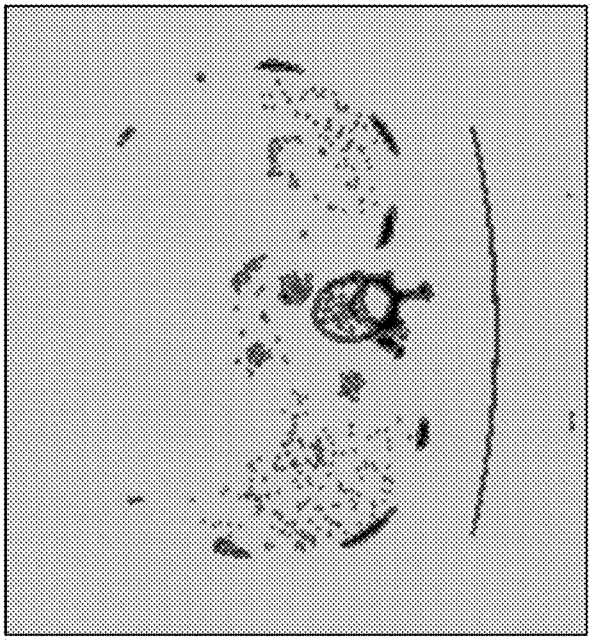

Step 1130: Searching the input image for a plurality of third pixels satisfying a second condition to obtain a fourth image. In some embodiments, when the first feature value is the median value or the average grayscale value of the first pixels, the first condition is, for example, less than the first feature value F multiplied by a predetermined threshold T2 (i.e., "<(F×T2)"). That is, the image post-processing module 135 searches the input image for the second pixels with grayscale values less than the first feature value F multiplied by the predetermined threshold T2. In some other embodiments, when the first eigenvalue is the gradient or percentile of the first pixels, the first condition is, for example, the gradient or percentile less than the predetermined threshold T2. That is, the image post-processing module 135 searches the input image for second pixels with the gradient or percentile less than the predetermined threshold T2. For ease of description, the first feature value is the average grayscale value of the pixels, and the fourth image is shown in FIG. 12C.

Step 1140: Subtracting the third image and the fourth image from the input image to obtain a fifth image. For example, when the first feature value is the average grayscale value of the first pixels, in steps 1120 and 1130, the input image is searched for the second pixels with higher grayscale values and the third pixels with lower grayscale values. Accordingly, when the third image and the fourth image are subtracted from the input image, the remaining pixels will have grayscale values similar to those of the target organ, and the fifth image is shown in FIG. 12D.

Figure 12E:
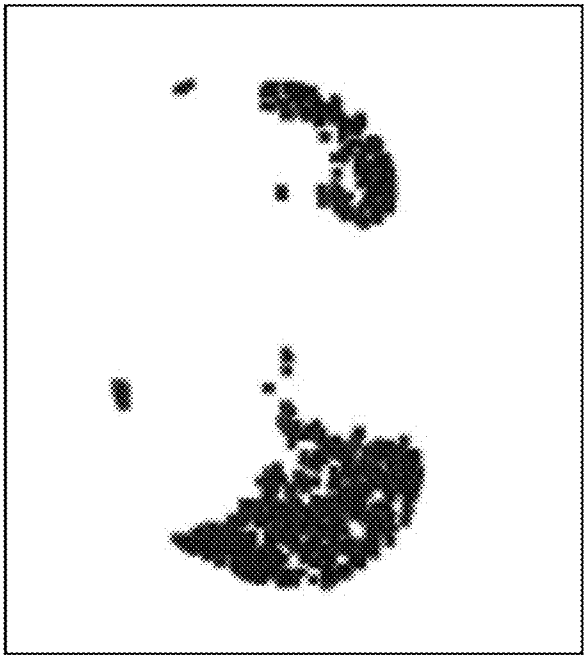
Figure 12F:
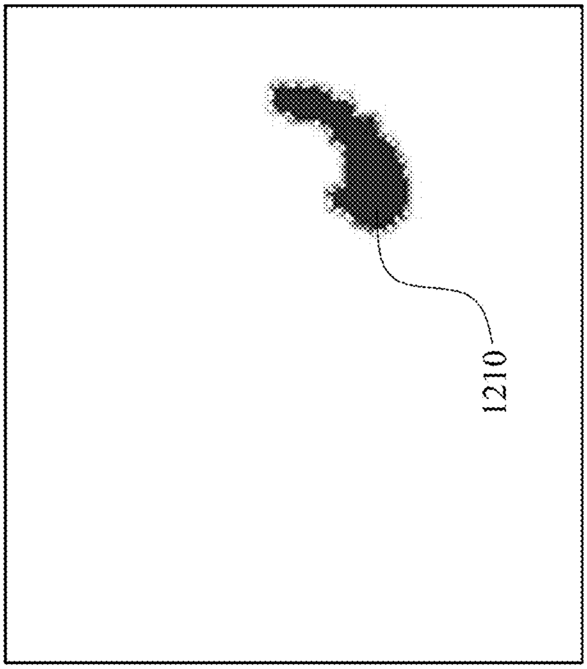
Figure 12G:
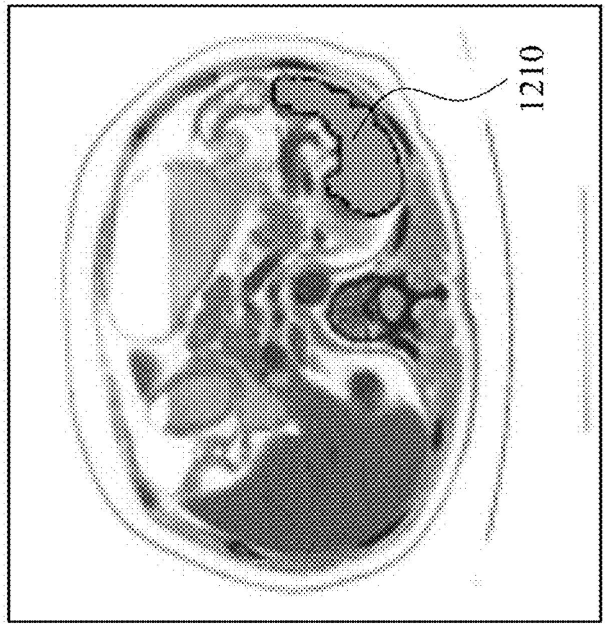

Step 1150: Performing watershed image processing on the fifth image to obtain a sixth image. A watershed algorithm is a type of conversion defined based on a grayscale image, and can be used for image segmentation. For example, the watershed algorithm can recognize a local grayscale minima or global grayscale minima in the fifth image, and use the similarity between neighboring pixels as a reference to connect pixels that are spatially close and have similar grayscale values to form a closed contour. The sixth image is shown in FIG. 12E. Accordingly, it can be seen that there are many closed profiles in FIG. 12E.

Step 1160: Selecting a region overlapping with the predicted mask from the sixth image to obtain a target region image. For example, the predicted mask generated by the artificial intelligence model 134 can be considered as the preliminary predicted result of the organ position, and the predicted mask may still include surrounding tissues of the target organ. Accordingly, it is not possible to accurately segment the image region of the target organ from the input mage based solely on the predicted mask. In addition, through processing of steps 1110 to 1150, pixels that are close to the target organ position and have similar grayscale values can be obtained from the input image, and then the contour of the target organ can be obtained through the watershed image processing. Accordingly, the image post-processing module 135 selects the region overlapping with the predicted mask from the sixth image to obtain the target region image, and the target region image can more accurately represent the position of the target organ, as shown by region 1210 in FIG. 12F.

Step 1170: Superimposing the target region image onto the input image to obtain the output image. For example, the target region image obtained in step 1160 represents the position of the target organ, but does not include other pixels outside the target organ. Accordingly, the image post-processing module 135 superimposes the target region image onto the input image to obtain the output image, allowing the medical personnel to clearly view the area of the recognized target organ on the input image. That is, the image post-processing module 135 superimposes region 1210 (i.e., target region image) in FIG. 12F onto the input image in FIG. 12A to obtain the output image in FIG. 12G, and the host 10 can display the output image in FIG. 12G on the display device 20. It should be noted that through the methods in FIG. 9 to FIG. 11, the artificial intelligence model 134 trained in the present disclosure can accurately recognize the position of abdominal organs or another organs from medical images, and the processor 110 can also calculate an actual volume corresponding to a target region image, allowing the medical personnel to determine whether there is a swelling in the target region image. In addition, the processor 110 can also use the output image to calculate homogeneity and heterogeneity of the human body tissue in the target region image, allowing the medical personnel to determine whether there is a tumor in the target region image.

Although the present disclosure is described above with preferred embodiments, the embodiments are not intended to limit the scope of the present disclosure. Any person of ordinary skill in the art may make variations and modifications without departing from the spirit and scope of the present disclosure. The protection scope of the disclosure should be subject to the appended claims.

What is claimed is:

1. A computer device, comprising:

a storage device, configured to store an image pre-processing application and an artificial intelligence model; and a processor, configured to execute the image pre-processing application and the artificial intelligence model to perform the following operations:

obtaining a first image set, wherein the first image set comprises at least two images captured with different parameters;

performing image pre-processing on each image of the first image set to obtain a second image set;

performing image augmentation on the second image set to obtain a third image set;

adding the third image set to a training image data set;

training the artificial intelligence model using the training image data set;

receiving an input image;

performing image pre-processing on the input image to obtain a first image;

utilizing the artificial intelligence model to recognize the first image to obtain a second image;

searching the input image for a plurality of first pixels corresponding to a position of a predicted mask in the second image, and calculating a first feature value of the first pixels;

searching the input image for a plurality of second pixels satisfying a first condition to obtain a third image;

searching the input image for a plurality of third pixels satisfying a second condition to obtain a fourth image;

subtracting the third image and the fourth image from the input image to obtain a fifth image;

performing watershed image processing on the fifth image to obtain a sixth image;

selecting a region overlapping with the predicted mask from the sixth image to obtain a target region image; and superimposing the target region image onto the input image to obtain the output image.

2. The computer device according to claim 1, wherein the at least two images are at least two medical images obtained by photographing the same body part of the same patient during substantially the same time interval using different parameters, and comprise corresponding labeled organ regions.

3. The computer device according to claim 1, wherein the image pre-processing comprises coordinate system conversion processing, locus-to-mask processing, image padding processing, image normalization processing, or a combination thereof.

4. A deep learning method of an artificial intelligence model for medical image recognition, the method comprising:

obtaining a first image set, wherein the first image set comprises at least two images captured with different parameters;

performing image pre-processing on each image of the first image set to obtain a second image set;

performing image augmentation on the second image set to obtain a third image set;

adding the third image set to a training image data set;

training the artificial intelligence model using the training image data set;

receiving an input image;

performing image pre-processing on the input image to obtain a first image;

utilizing the artificial intelligence model to recognize the first image to obtain a second image;

searching the input image for a plurality of first pixels corresponding to a position of a predicted mask in the second image, and calculating a first feature value of the first pixels;

searching the input image for a plurality of second pixels satisfying a first condition to obtain a third image;

searching the input image for a plurality of third pixels satisfying a second condition to obtain a fourth image;

subtracting the third image and the fourth image from the input image to obtain a fifth image;

performing watershed image processing on the fifth image to obtain a sixth image;

selecting a region overlapping with the predicted mask from the sixth image to obtain a target region image; and superimposing the target region image onto the input image to obtain the output image.

5. The method according to claim 4, wherein the at least two images are at least two medical images obtained by photographing the same body part of the same patient during substantially the same time interval using different parameters, and comprise corresponding labeled organ regions.

6. The method according to claim 4, wherein the image pre-processing comprises coordinate system conversion processing, locus-to-mask processing, image padding processing, image normalization processing, or a combination thereof.

* * * * *